(12) United States Patent
Birkenbach et al.

(10) Patent No.: US 9,818,175 B2
(45) Date of Patent: Nov. 14, 2017

(54) REMOVING IMAGE DISTORTIONS BASED ON MOVEMENT OF AN IMAGING DEVICE

(71) Applicant: Brainlab AG, Munich (DE)

(72) Inventors: Rainer Birkenbach, Erding (DE); Dieter Ceglarz, Munich (DE); Till Gerken, Wiesbaden (DE)

(73) Assignee: Brainlab AG, Munich (DE)

( * ) Notice: Subject to any disclaimer, the term of this patent is extended or adjusted under 35 U.S.C. 154(b) by 38 days.

(21) Appl. No.: 14/652,290

(22) PCT Filed: Dec. 17, 2012

(86) PCT No.: PCT/EP2012/075679
§ 371 (c)(1),
(2) Date: Jun. 15, 2015

(87) PCT Pub. No.: WO2014/094811
PCT Pub. Date: Jun. 26, 2014

(65) Prior Publication Data
US 2015/0302556 A1    Oct. 22, 2015

(51) Int. Cl.
*G06K 9/00*    (2006.01)
*G06T 5/00*    (2006.01)
(Continued)

(52) U.S. Cl.
CPC ............ *G06T 5/00* (2013.01); *G06F 19/3406* (2013.01); *G06T 5/006* (2013.01); *G06T 7/33* (2017.01);
(Continued)

(58) Field of Classification Search
CPC ....... G06F 19/3406; G06T 5/00; G06T 5/006; G06T 7/0028; G06T 7/004;
(Continued)

(56) References Cited

U.S. PATENT DOCUMENTS

| | | | | |
|---|---|---|---|---|
| 6,490,473 B1 * | 12/2002 | Katznelson | ............ | A61B 5/055 600/410 |
| 2010/0246767 A1 * | 9/2010 | Tanabe | ................. | A61N 5/1049 378/65 |

(Continued)

FOREIGN PATENT DOCUMENTS

| | | |
|---|---|---|
| DE | 10323008 | 12/2004 |
| WO | 2008039793 | 4/2008 |

OTHER PUBLICATIONS

European Patent Office, International Search Report, dated Jun. 12, 2013, pp. 1-4, European Patent Office, Rijswijk, The Netherlands.

*Primary Examiner* — Amara Abdi
(74) *Attorney, Agent, or Firm* — Middleton Reutlinger

(57) ABSTRACT

A data processing method of determining a transformation for transforming medical image data into a positional reference system, the method being executed by a computer and comprising the following steps: a) acquiring reference position data comprising reference position information describing a reference position of a medical imaging apparatus in an imaging apparatus reference system; b) acquiring imaging geometry data comprising imaging geometry information describing an imaging geometry of the medical imaging apparatus; c) acquiring actual position data comprising actual position information describing different actual positions of the medical imaging apparatus in an imaging apparatus reference system, wherein the medical imaging apparatus takes the actual positions for acquiring medical image data comprising medical image information describing an image of the anatomical region of the patient's body at each of the actual positions; d) determining, based on the reference position data and the imaging geometry data and the actual position data, medical image transformation data comprising medical image transformation information describing a medical image transformation between (Continued)

the actual position of the medical imaging and the reference position.

11 Claims, 1 Drawing Sheet

(51) Int. Cl.
    *G06F 19/00*     (2011.01)
    *G06T 7/33*     (2017.01)
    *G06T 7/70*     (2017.01)

(52) U.S. Cl.
    CPC ...... *G06T 7/70* (2017.01); *G06T 2207/10081* (2013.01); *G06T 2207/10088* (2013.01); *G06T 2207/20201* (2013.01); *G06T 2207/30096* (2013.01)

(58) Field of Classification Search
    CPC . G06T 2207/10081; G06T 2207/10088; G06T 2207/20201; G06T 2207/30096
    See application file for complete search history.

(56) References Cited

U.S. PATENT DOCUMENTS

| | | | |
|---|---|---|---|
| 2011/0026666 A1* | 2/2011 | Nijhof | A61B 6/12 378/8 |
| 2014/0120493 A1* | 5/2014 | Levin | A61C 9/0066 433/29 |
| 2014/0246606 A1* | 9/2014 | Yajima | G21K 5/10 250/492.3 |

* cited by examiner

REMOVING IMAGE DISTORTIONS BASED ON MOVEMENT OF AN IMAGING DEVICE

The present invention is directed to a method, in particular a data processing method of determining a transformation for transforming medical image data into a positional reference system in accordance with claim 1, a corresponding computer program, computer executing the program and program storage medium storing the program as well as a signal wave carrying information representing the program. Furthermore, the invention is directed to a system, in particular navigation system, for an image-guided medical procedure, the system comprising the aforementioned computer.

Many medical procedures, in particular image-guided medical procedures such as navigated interventions on the human body, involve taking a sequence of medical images of an anatomical region of the patient's body. For some applications, mobile scanners such as mobile CT scanners or x-ray scanners (such as C-arcs) are used to generate the medical image data. Such a mobile scanner in general does not have a fixed position relative to a bed on which the patient to be imaged is placed. Thus, when moving the scanner for taking the sequence of medical images, deviations of the isocentre of the scanner from an ideal trajectory along which the medical images are taken may cause undesired distortions of the medical image information when comparing different medical images of one sequence. Such deviations from the ideal trajectory may be due to for example unevenness of the ground on which the scanner is moved while taking the sequence. Another reason for the deviations may for example be an angled placement of the patient with regard to the ideal trajectory.

Known methods of removing the undesired image distortion include reconstruction of an in particular three-dimensional image volume from several single images which are distributed across the scan volume in space while recording the image sequence. However, such a procedure is computationally expensive.

A problem to be solved by the invention therefore is to find an efficient way of removing image distortions caused by moving a mobile medical imaging device along a trajectory which deviates from an ideal trajectory.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. Examples of analytical devices include x-ray machines, computer tomographs and magnetic resonance tomographs. The imaging methods are in particular used for medical diagnostics, to analyze the anatomical body (anatomical regions of a patient's body) in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumors are for example usually visible on MRI scans when contrast agents are used to infiltrate the tumour. The MRI scans represent an example of an imaging method. In the case of MRI scans of such brain tumors, the signal enhancement in the MRI images (due to the contrast agents infiltrating the tumour) is considered to represent the solid tumour mass. Thus, the tumour is detectable and in particular discernable in the image generated by the imaging method.

The method in accordance with the invention is in particular a data processing method. The data processing method is preferably performed using technical means, in particular a computer. Preferably, the inventive method is at least partly executed by a computer. That is, all steps or just some of the steps (i.e. less than a total number of steps) of the inventive method may be executed by a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (BC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

The invention also relates to a navigation system for a navigated, in particular computer-assisted medical procedure, comprising:

the computer of the preceding claim, for processing the reference position data, imaging geometry data and actual position data;

a detection device for detecting the position of the medical imaging apparatus in order to generate at least one of the actual position data and the reference position data and to supply the actual position data to the computer;

a data interface for receiving at least one of the actual position data and the reference position data and for supplying the at least one of the actual position data and the reference position data to the computer; and a user interface for receiving data from the computer in order to provide information to the user, wherein the received data are generated by the computer on the basis of the results of the processing performed by the computer.

The method in accordance with the invention is preferably a data processing method of determining a transformation for transforming medical image data into a positional reference system. A positional reference system is understood to encompass (i.e. comprise or consist of) a coordinate system in which positions can be defined by tuples of coordinates in in particular two or three dimensions. A position is an abstract entity and is preferably defined relative to an origin of the positional reference system. The coordinates used for defining a position in a specific positional reference system may be any kind of coordinates which are suitable for the specific application, for example coordinates on orthogonal axes such as Cartesian coordinates, or spherical coordinates in three dimensions or two dimensions (in particular, two-dimensional polar coordinates). Furthermore, a positional reference system may be defined to rest relative to an abstract or real entity. For example, a positional reference system may be defined to rest relative to an apparatus (for example, a medical instrument or a medical imaging device) or relative to a global coordinate system. Alternatively, a positional reference system may be defined to be moving relative to a real entity (such as a medical instrument or medical imaging device) or an abstract entity (such as another coordinate system, in particular a global coordinate system in which the position of the origin of the specific reference system is defined).

Preferably, reference position data is acquired which comprises reference position information. The reference position information in particular describes, more particularly represents a reference position of a medical imaging apparatus in an imaging apparatus reference system. The imaging apparatus reference system preferably is a positional reference system in which the imaging apparatus moves (i.e. is able to move), in particular the origin of the imaging apparatus reference system is defined not to lie in a component of the medical imaging apparatus. The reference position of the medical imaging apparatus is preferably determined by detection of markers, in particular a marker device, having a predetermined and preferably fixed position relative to the medical imaging apparatus.

It is the function of a marker to be detected by a marker detection device (for example, a camera or an ultrasound receiver or analytical devices, like CT), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or more than one (individual) markers which are preferably in a predetermined spatial relationship. A marker device comprises one, two, three or more markers which are in case of two or more markers in a predetermined spatial relationship. This predetermined spatial relationship is in particular known to a navigation system and for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

For example, a navigation system detects optical signals which are reflected by pieces of retroreflective marker foil attached to the medical imaging apparatus at in particular discrete positions on the medical imaging apparatus. For example, if the medical imaging apparatus is a CT scanner, the pieces of marker foil may be distributed along the circumference of the scanner tunnel, thereby preferably also defining an isocentre of the CT scanner. The isocentre is understood to be defined as a point (or set of points) and/or volume in space which, regardless of orientation of the beam source of the scanner relative to the longitudinal moving direction of the scanner, remains in the focus of the imaging beam and is therefore always imaged in any possible beam source position. Alternatively or additionally, the imaging apparatus reference system may be defined as a global reference system, in which the medical imaging apparatus can move. Such a global reference system is preferably defined to be a positional reference system which rests relative to another physical entity, for example relative to a camera of the navigation system.

Preferably, imaging geometry data is acquired which comprises imaging geometry information. The imaging geometry information in particular describes, more particularly represents, an imaging geometry of the medical imaging apparatus.

Preferably, the imaging geometry information describes the position of an imaging plane of the medical imaging apparatus relative to the medical imaging apparatus. The position of the imaging plane is in particular determined based on detecting a marker device having a predetermined, in particular fixed, position relative to the anatomical region. Alternatively, the position of the imaging plane is determined based on the imaging isocentre data comprising imaging isocentre information describing the position of an imaging isocentre of the medical imaging apparatus relative to the medical imaging apparatus.

The imaging geometry information preferably comprises information which allows the analysis image (x-ray image) to be calculated, given a known relative position between the imaging geometry analysis apparatus and the analysis object (anatomical body part) to be analyzed by the x-ray radiation, if the object (anatomical body part) to be analyzed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The position and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (in particular, the orientation) and the shape (for example, a conical shape exhibiting a specific angle of inclination) of said multiplicity (manifold). The position can in particular be represented by the position of an x-ray beam which passes through the centre of said multiplicity or by a position of a geometric object (such as a truncated cone) which represents the multiplicity (manifold) of x-ray beams.

Information concerning the above-mentioned interaction is preferably three-dimensionally known, for example from a three-dimensional CT, and describes the interaction in a spatially resolved way for points and/or regions of the analysis object, in particular force all of the points and/or regions of the analysis object. Knowledge of the imaging geometry in particular allows a location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery"
4. EP 08 156 293.6
5. U.S. 61/054,187

Preferably, actual position data is acquired which comprises actual position information. The actual position information in particular describes, more particularly represents, different actual positions of the medical imaging apparatus relative to an anatomical region of a patient's body which is to be imaged. The actual position information is preferably acquired based on knowledge about the relative position of the isocentre of the medical imaging apparatus relative to the medical imaging apparatus and/or knowledge of the position of the isocentre in the imaging apparatus reference system. As the medical imaging apparatus only images objects which are located in the isocentre, the different actual position of the medical imaging apparatus relative to the anatomical region which is actually imaged can be determined based on such knowledge (information). Alternatively, the actual position information may be determined based on detecting the position of the medical imaging apparatus relative to the anatomical region based on tracking markers having a predetermined and preferably fixed position relative to the medical imaging apparatus and tracking markers having a predetermined and preferably fixed position relative to the anatomical region. For example, in addition to the markers attached to the medical imaging apparatus, markers and/or marker devices may be attached to the patient's body such that they have a predetermined and preferably fixed position relative to the anatomical region. Preferably, the medical imaging apparatus takes the actual positions for (in particular, while) acquiring medical image data comprising medical image information. The medical image information in particular describes, more particularly represents an image of the anatomical region of the patient's body at each of the actual positions. The medical imaging apparatus is moved relative to the patient's body for taking at least one image at each of the actual positions. Such a movement is in this disclosure termed "imaging movement". For example, the tunnel of a CT scanner is moved relative to a longitudinal (cranial-caudal) axis of the patient's body while the images are taken. The medical imaging apparatus in particular does not have a predetermined (in particular, a fixed) position relative to the patient's body and/or a patient support device such as a bed on which the patient rests during that movement. For example, the medical imaging apparatus is an independent mobile unit which may be used and moved separately from and independently of the patient support device. Examples of such a medical imaging apparatus encompass a mobile MR scanner and a mobile CT scanner which move on a chain drive or on wheels.

As the position of the medical imaging apparatus relative to the anatomical region during movement of the medical imaging apparatus is not predetermined, a spatial transformation, i.e. a mapping, from the position of the medical imaging apparatus to the position of the anatomical region in preferably a common positional reference system in which the positions of both the medical imaging apparatus and the anatomical region can be defined is preferably determined based on knowledge of the referenced position information and the actual position information. The reference position preferably is a predetermined position. As such a predetermined position in particular a start position of the medical imaging apparatus may be used, the start position being the position of the medical imaging apparatus before it is moved for acquisition for the medical image data, in particular for acquisition of a sequence of medical images of the anatomical region. According to a preferred embodiment, the reference position is the position of the medical imaging apparatus in the positional reference system in which it is tracked (in particular, the imaging apparatus reference system) by a navigation system in particular when the first medical image of the sequence is taken. It is notable that taking the medical images is not necessarily part of the present invention, as the present invention focuses on determining a positional transformation rather than taking medical images.

According to an embodiment of the invention, the reference position information describes, in particular represents, a reference trajectory of the medical imaging apparatus. For example, the medical imaging apparatus is moved along the trajectory along which it is to be moved for taking the sequence of medical images in a test run and tracked during that movement. Thereby, a reference trajectory of the medical imaging apparatus describing a sequence of reference positions of the medical imaging apparatus in the imaging apparatus reference system is acquired.

Preferably, medical image transformation data is determined based on the reference position data (in particular, the reference position information) and the imaging geometry data (in particular, the imaging geometry information) and the actual position data (in particular, the actual position information). The medical image transformation data comprises medical image transformation information which in particular describes, more particularly represents, a transformation (in particular, a coordinate transformation) between the actual position of the medical imaging apparatus and the reference position. This transformation is applied in particular to medical image information and thus also called "medical image transformation". The transformation in particular is a mapping between the actual position and the reference position in a common positional reference system in which both the actual position and the reference position can be, in particular are, defined. The common positional reference system according to an embodiment of the invention is the imaging apparatus reference system. Alternatively, the common positional reference system may be a patient-centered reference system, i.e. a positional reference system which rests relative to the patient's body.

The medical image transformation in particular is suitable for removing the effect of a change of position of the medical imaging apparatus during the imaging movement from the medical images taken during the imaging movement. Preferably, the medical image transformation data is determined based on information about the difference in anyone of components, in particular its vertical component, of the reference position and the corresponding component, in particular the vertical component, of the actual position, wherein the horizontal is defined in particular as being parallel to the plane in which the medical imaging apparatus is moved during the imaging movement. In particular, the vertical component is defined to be vertical relative to the movement direction of the medical imaging apparatus. The medical image transformation may therefore be set to comprise a deviation vector describing a deviation of the actual position from the reference position. In general, the deviation vector is non-zero for anyone of its components.

Preferably, a visual indicating device or audio indicating device of the navigation system used to track the imaging apparatus is configured to determine warning data comprising warning information describing a warning that is to be issued if the medical image transformation information reaches a predetermined value, in particular if a difference in at least one dimension between the referenced position and the actual position reaches a predetermined value. The inventive method therefore preferably comprises the step of the determining such warning data and issuing a corresponding (visual and/or audio) warning. For example, a threshold value for a deviation of the actual position from the reference position in the vertical direction may be predetermined and acquired by the inventive method and the medical image transformation evaluated as to a difference in the respective component between the actual position and the reference position represented by the transformation. The present invention is not limited to evaluating a difference in the vertical direction. Rather, it is within the framework of the invention to evaluate a difference between at least one dimensional component of the reference position (e.g., one, two or three components—as an example, in the y- and z-components) and at least one corresponding dimensional component of the actual position (ion this example, the y- and z-components). If a difference in more than one component is evaluated, the overall difference is preferably determined as a mean (i.e. average or root-mean-square) value of the difference in each individual component. That difference may then be compared to the threshold value and, if the comparison results in that the determined difference has a particular relationship to the predetermined (threshold) value, in particular is larger than the predetermined value, issuing a warning based on the warning information. The warning may be issued as audio output or visual output which may then be recognized by an operator. Such a feature supports avoiding taking medical images which are associated with too large a positional deviation of the medical imaging apparatus compared to the reference position. Thereby, complications in mapping the medical image data into a common reference system and superfluous radiation exposure of the patient may be avoided.

Instead of or additionally to markers (at least one marker device) having a predetermined position relative to the medical imaging apparatus, an internal position change determination unit of the medical imaging apparatus such as a gyroscope may be used for acquiring gyroscope data (as the actual position data) comprising gyroscope information (as the actual position information). The gyroscope information in particular describes, more particularly represents, the actual position of the medical imaging apparatus in the imaging apparatus reference system. The gyroscope is configured to measure the actual position and preferably has a predetermined, in particular fixed, position to the medical imaging apparatus. Using a gyroscope may, compared to using emitting or reflecting markers, lead to an increased accuracy of the reference position information and actual position information, thereby leading to a higher accuracy in determining the medical image transformation data. Alternatively or additionally, other internal position change determination units such as at least one of an accelerometer (in particular, a three-dimensional accelerometer) and a pressure sensor (which is in particular attached to a moving mechanism of the medical imaging apparatus such as a set of wheels) may be used to determine an unevenness of the floor on which the medical imaging apparatus. Information acquired from such internal position change determination units is preferably used to drive a position change mechanism of the medical imaging apparatus to change is position relative to the anatomical region based on the medical image transformation data such that the actual position becomes equal or approximately equal to the reference position. If an internal position determination unit is used, an initial position of the medical imaging apparatus should preferably be predetermined or determined by other means, e.g. by using optical tracking.

In the following, an example embodiment of the invention is described with reference to the Figures which are merely to be regarded as examples of the invention without limiting the invention to the specific embodiment.

Figure 1:
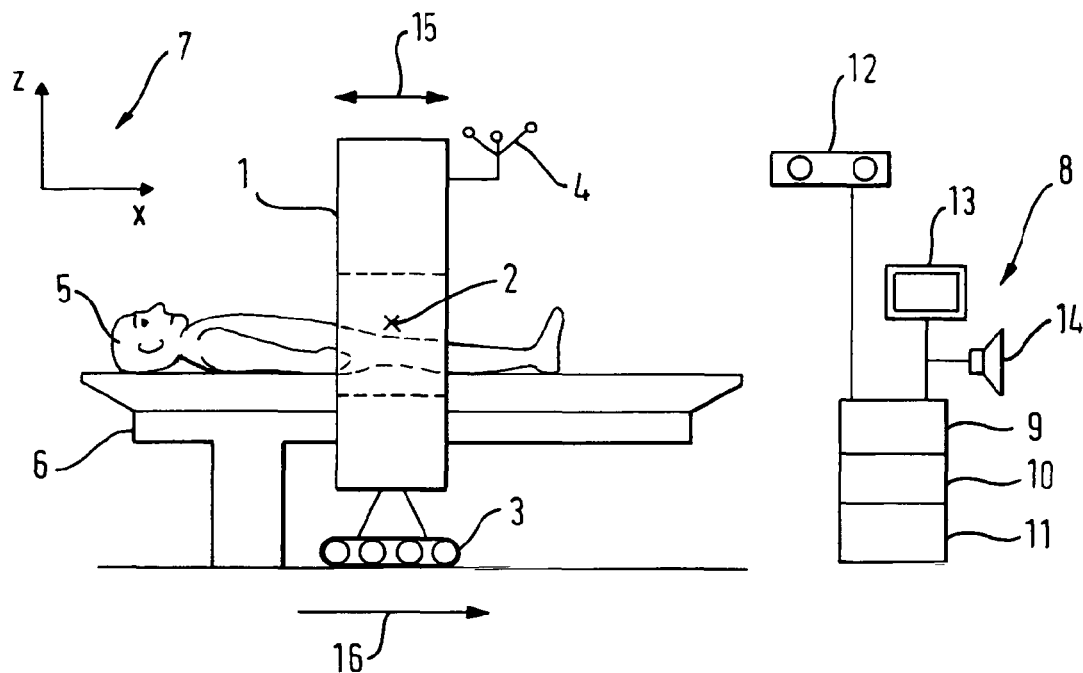
FIG. 1 shows a general setup of a mobile CT scanner which is tracked by a navigation system and placed in position for imaging an anatomical region.

In FIG. 1, a mobile CT scanner 1 which is movable on a set of tracks 3 and comprises an imaging isocenter 2 is placed ready for imaging an anatomical region of a patient 5 who is placed on a bed 6. A reference star 4 is attached to the CT scanner 1 and is tracked by a detection device embodied by a stereotactic camera 12 of a navigation system 8. The navigation system 8 also comprises a computer having a digital processor 9, a volatile memory embodied by a RAM 10 and a non-volatile memory embodied by a hard disc 11. Furthermore, the navigation system 8 comprises a monitor 13 and a loudspeaker 14 as visual and audio indicating devices which are associated with the computer comprising the processor 9, the RAM 10 and the hard disc 11. Also depicted in FIG. 1 is an imaging apparatus reference system 7 showing the directions of an x- and z-axis, wherein the CT scanner 1 can be moved in the positive and the negative x-direction as indicated by the double arrow 15. Due to an unevenness of the floor, the position of the CT scanner will during such a movement also vary in the z-direction.

Figure 2:
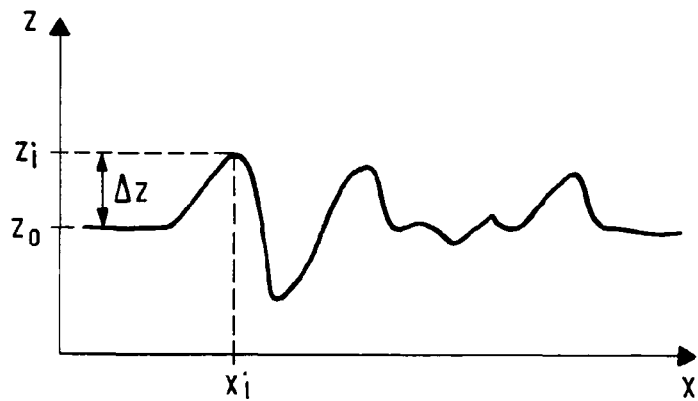
FIG. 2 shows a reference curve for deviations of the vertical position of the CT scanner isocenter when moved along the x-direction of FIG. 1.

FIG. 2 shows a curve representing the movement of the CT scanner isocenter 2 in the z-direction when moved along the x-direction as indicated by the arrow 16 in FIG. 1. The curve shown in FIG. 2 is a reference profile representing a reference trajectory in the z-direction which was acquired by tracking the movement of the CT scanner 1 with a navigation system 8 by detection of the position of the markers contained in the reference star 4. For each position $x_i$ at which the anatomical region of the patient's body is imaged by the CT scanner 1, the position value $z_i$ of the CT scanner 1 or the imaging isocenter 2, respectively, in the z-direction (which in this case is the vertical direction) is corrected to the normal z-level $z_0$ representing the reference position in the z-direction which is defined as the z-position of the CT scanner 1 or the imaging isocenter 2, respectively, at the beginning of the curve of FIG. 2. The embodiment shown in the Figures therefore reduces the measured $z_i$ value by $\Delta z$ to the reference position $z_0$. Thereby, the position of the imaging isocentre 2 is corrected to lie at the reference level $z_0$ and based on this correction and information about the imaging geometry of the CT scanner 1, the medical image transformation information is determined by the computer of the navigation system 8. This medical image transformation information is then used to transform the medical image data taken by the CT scanner 1 into a common perspective which is common to all of the images taken in an imaging sequence during movement of the CT scanner 1 along the longitudinal axis of the patient's body in the x-direction.

The invention claimed is:

1. A method of determining a transformation for projecting medical image data onto a reference position of an imaging isocentre of a medical imaging apparatus, the method executed by computer and comprising the following steps:
    acquiring imaging isocentre reference trajectory data describing a reference trajectory of the imaging isocentre of the medical imaging apparatus, wherein the reference trajectory is a sequence of predetermined reference positions of the imaging isocentre;
    acquiring imaging isocentre actual position data describing an actual position of the imaging isocentre of the medical imaging apparatus from Which the medical imaging apparatus acquires medical image data describing an image of an anatomical region of a patient's body;
    acquiring imaging geometry data describing an imaging geometry of the medical imaging apparatus;
    determining, based on the imaging isocentre reference trajectory data and the imaging isocentre actual position data, isocentre position difference data describing a difference between the actual position and a corresponding reference position, wherein the corresponding reference position is included in the sequence of predetermined reference positions;
    determining, based on the isocentre position difference data, whether the difference constitutes a deviation of the actual position from the corresponding reference position; and
    if the immediately prior determining step results in that the difference constitutes a deviation of the actual position from the corresponding reference position, correcting the medical image data by determining, based on the imaging geometry data and the medical image data and the isocentre position data, image transformation data describing a transformation for projecting the medical image data acquired from the actual position into a representation corresponding to the case of the medical image data having been acquired from the corresponding reference position, and applying the transformation to the medical image data taken from the actual position.

2. The method according to claim 1, wherein the imaging geometry data describes the position of an imaging plane of the medical imaging apparatus relative to the medical imaging apparatus, wherein the position of the imaging plane is determined based on detecting a marker device having a predetermined position relative to the anatomical region or based on imaging isocentre data comprising imaging isocentre information describing the position of an imaging isocentre of the medical imaging apparatus relative to the medical imaging apparatus.

3. The method according to claim 1, wherein the medical imaging apparatus is an X-ray-based CT scanner or an MR scanner.

4. The method according to claim 1, wherein the image transformation data is determined based on information about the difference in at least one dimensional component of the reference trajectory and at least one corresponding dimensional component of the actual position.

5. The method according to claim 1, wherein the actual position data is acquired based on detecting the position of at least one marker device having a predetermined position relative to the medical imaging apparatus.

6. The method according to claim 5, wherein the position of the marker device is determined based on detecting electromagnetic radiation emitted or reflected from the marker device.

7. The method according to claim 1, comprising a step of determining warning data comprising warning information describing a warning that is to be issued if the image transformation data reaches a predetermined value.

8. The method according to claim 1, wherein the actual position data is acquired based on measurements taken by an internal position determination unit of the medical imaging apparatus having a predetermined position relative to the medical imaging apparatus.

9. A non-transitory computer-readable program storage medium storing a program which, when running on a processor of a computer or when loaded into the memory of a computer, causes the computer to determine a transformation for projecting medical image data onto a reference position of a medical imaging apparatus, the computer operable to:

acquire imaging isocentre reference trajectory data describing a reference trajectory of the imaging isocentre of the medical imaging apparatus, wherein the reference trajectory is a sequence of predetermined reference positions of the imaging isocentre;

acquire imaging isocentre actual position data describing an actual position of the imaging isocentre of the medical imaging apparatus from which the medical imaging apparatus acquires medical image data describing an image of an anatomical region of a patient's body;

acquire imaging geometry data describing an imaging geometry of the medical imaging apparatus;

determine, based on the imaging isocentre reference trajectory data and the imaging isocentre actual position data, isocentre position difference data describing a difference between the actual position and a corresponding reference position, wherein the corresponding reference position is included in the sequence of predetermined reference positions;

determine, based on the isocentre position difference data, whether the difference constitutes a deviation of the actual position from the corresponding reference position; and if the immediately prior determining step results in that the difference constitutes a deviation of the actual position from the corresponding reference position, correcting the medical image data by determining, based on the imaging geometry data and the medical image data and the isocentre position data, image transformation data describing a transformation for projecting the medical image data acquired from the actual position into a representation corresponding to the case of the medical image data having been acquired from the corresponding reference position, and applying the transformation to the medical image data taken from the actual position.

10. A computer operably coupled to the non-transitory computer-readable program storage medium of claim 9.

11. A navigation system for a medical procedure, comprising:

the computer of claim 10 for processing the imaging isocentre reference trajectory data, the medical image data, the imaging geometry data, the imaging isocentre actual position data, the isocentre position difference data, and the image transformation data;

a detection device for detecting the actual position of the medical imaging apparatus; and a data interface for receiving, from the detection device, at least one signal corresponding to the imaging isocentre actual position data and a data interface for supplying the imaging isocentre actual position data to the computer.

* * * * *